United States Patent [19]

Vinson

[11] 4,180,561
[45] Dec. 25, 1979

[54] HAIR PRESSING COMPOSITION

[76] Inventor: William L. Vinson, 6145 Vine St., Philadelphia, Pa. 19139

[21] Appl. No.: 761,044

[22] Filed: Jan. 21, 1977

[51] Int. Cl.$^2$ .............................................. A61K 7/09
[52] U.S. Cl. ...................................... 424/71; 424/70; 424/74
[58] Field of Search ............................ 424/70, 71, 74

[56] References Cited

U.S. PATENT DOCUMENTS

| 2,541 | 4/1842 | Mackay | 424/74 |
|---|---|---|---|
| 75,806 | 3/1868 | Stearns | 424/74 |
| 1,350,843 | 8/1920 | Roman | 424/74 |
| 3,932,611 | 1/1976 | McCarthur | 424/70 |

FOREIGN PATENT DOCUMENTS

| 704195 | 2/1965 | Canada | 424/74 |
|---|---|---|---|
| 745988 | 11/1966 | Canada | 424/74 |
| 967058 | 3/1950 | France | 424/74 |
| 1268459 | 6/1961 | France | 424/74 |
| 1489266 | 6/1967 | France | 424/74 |
| 179254 | 8/1935 | Switzerland | 424/74 |
| 2851 | of 1897 | United Kingdom | 424/74 |
| 350064 | 6/1931 | United Kingdom | 424/74 |

OTHER PUBLICATIONS

Chemical Abstracts, vol. 48, column 10138b, (1954).
Thomas, A Dictionary of Terms in Pharmacognosy, Charles C. Thomas Publisher, Springfield, Illinois (1955), p. 63.
Lucas, Nature's Medicines, Wilshire Book Company, Hollywood, California (1971), pp. 78-79 and 173.

*Primary Examiner*—James O. Thomas, Jr.
*Assistant Examiner*—Vera C. Clarke
*Attorney, Agent, or Firm*—Seidel, Gonda, Goldhammer & Panitch

[57] ABSTRACT

A hair pressing composition is provided comprising a base of petrolatum and lanolin having an effective amount of active ingredients comprising a mixture of weeping willow extract and an extract from mustard greens and corn. The petrolatum is preferably white petrolatum present in about 32 parts by volume and the lanolin is preferably anhydrous lanolin present in an amount of about 24 to about 32 parts by volume. Each of the active ingredients is preferably present from about 4 to about 8 parts by volume.

12 Claims, No Drawings

HAIR PRESSING COMPOSITION

BACKGROUND OF THE INVENTION

This invention pertains to a novel hair pressing composition which is substantially greaseless in application and which possesses the characteristics of making hair easy to handle and of holding hair in a straight or curled condition, as desired.

Various compositions of hair setting preparations are known in the prior art. Most of these preparations are used to impart sheen, luster and body to the hair, while at the same time holding the hair in a particularly set style.

The prior art has experienced a problem in providing a hair setting composition which imparts the proper setting properties to hair and which does not have a greasy and oily appearance and feel. This greasy or oily appearance and feel has frequently been associated with hair preparations having a base of petrolatum and other mineral oils. Various attempts have been made to provide a hair preparation having good sheen, luster and body characteristics and to minimize the oily or greasy appearance and feel of the preparation.

U.S. Pat. No. 3,932,611 issued to McCarthur provides for a hair and scalp care cosmetic mixture comprising white petroleum jelly, along with beeswax, olive oil, castor oil, coconut oil, oil of sassaphras and perfuming agent. The patentee states that this preparation allows individual hair strands to be surrounded with a softening, oily moisture that complements the natural secretions of the hair follicles which contribute to soft and controllable hair. Loose dandruff particles are held in close proximity to the scalp because of the oily nature of the mixture. The beeswax contained in the mixture has a slight stiffening effect to aid in holding set curls and stylings without suppressing the natural resiliency of the hair.

U.S. Pat. No. 3,453,361 issued to Mendez discloses a hair preparation of the pomade or brilliantine type comprising a homogeneous solution of mineral oil and chicle. The chicle aids in holding the hair together and serves to tone down the oily or greasy appearance of pure mineral oil.

U.S. Pat. No. 3,949,764 of Scott describes a hair treating composition comprising a hardening and adhesive agent mixed with a flame-retardant agent in an aqueous medium. This composition is used to treat synthetic or natural hair to provide curling of straight hair or straightening of kinky hair. The composition is applied to the hair and dried at elevated temperatures after the hair has been styled as desired.

SUMMARY OF THE INVENTION

The present invention provides for a hair pressing composition useful in styling hair. By this, it is meant that straight hair can be curled, waved, etc. and that curly or kinky hair can be straightened by using the preparation of the present invention.

The hair pressing composition of the present invention comprises a base of petrolatum (petroleum jelly) and lanolin. Preferably, the petrolatum is white petrolatum and the lanolin is anhydrous lanolin. The base may contain other conventional ingredients, such as coconut oil, for example. The active ingredients of the present invention include an effective amount of weeping willow extract and the extract from a mixture of mustard greens and corn. Optional ingredients include glycerine, vinegar and wheat germ oil, as well as other conventional ingredients such as herbs, perfumes, coloring agents and the like.

DESCRIPTION OF THE PREFERRED EMBODIMENTS

A hair pressing composition according to the present invention comprises a base which is a mixture of petrolatum and lanolin. Preferably, the petrolatum is white petrolatum, present in an amount of about 32 parts by volume. The lanolin is preferably anhydrous lanolin, present in an amount of about 24 to about 32 parts by volume. Other vegetable oils, such as coconut oil, for example, may be added to the base. When coconut oil is added to the base, it is preferably present in an amount of up to about 4 parts by volume.

The active ingredients of a hair pressing composition according to the present invention include an effective amount of weeping willow extract and the extract from mustard greens and corn. It is presently preferred to have from about 4 to about 8 parts by volume each of the weeping willow extract and the extract from mustard greens and corn.

Various optional ingredients may be added to a hair pressing composition in accordance with the present invention. These optional ingredients include, among others, wheat germ oil in an amount of up to about 8 parts by volume, and preferably, in an amount of about 4 to about 8 parts by volume; glycerine in an amount up to about 1 part by volume; and vinegar in an amount of up to about 1 part by volume. Other optional ingredients include, for example, dandruff treating agents, coloring agents, various mixtures of herbs (e.g., sage, ginseng root, etc.), perfumes, and the like.

The weeping willow extract is prepared by splitting about 1 part by weight of weeping willow twigs, sticks or branches and placing the split weeping willow twigs, sticks or branches in about 20 parts by weight of water. The twigs are boiled in water until a solution of weeping willow juices in water, having the approximate color of tea is formed. The twigs are then removed from the solution which comprises the weeping willow extract. A suitable weeping willow extract has been formed by boiling about 3 ounces of split, chopped weeping willow twigs in about ½ gallon of water for about ½ hour.

The extract from mustard greens and corn is prepared as follows. About 2 parts by weight of mustard greens are mixed with 1 part by weight of corn kernels. This mixture is ground and then pressed to squeeze out the extract. Alternatively, juice can be expressed separately from 2 parts by weight of ground mustard greens and mixed with juice separately expressed from 1 part by weight of ground corn kernels.

The presently preferred hair pressing compositions according to the present invention will now be described in more detail with reference to the following specific, non-limiting examples:

EXAMPLE I

| Ingredient | Amount (fl. oz.) | Parts by Volume |
|---|---|---|
| White Petrolatum | 8 | 32 |
| Anydrous Lanolin | 6 | 24 |
| Coconut Oil | 1 | 4 |
| Weeping Willow Extract | 2 | 8 |
| Extract of Mustard Greens | | |

-continued

| Ingredient | Amount (fl. oz.) | Parts by Volume |
|---|---|---|
| and Corn | 2 | 8 |
| Glycerine | ¼ | 1 |
| Wheat Germ Oil (Viobin Brand) | ¼ | 1 |
| Vinegar | ¼ | 1 |

The base of the hair pressing composition in accordance with this example is prepared by placing the white petrolatum and the anhydrous lanolin in a vessel and melting them, while stirring, to form a homogeneous mixture. The coconut oil is beat into the lanolin-petrolatum mixture while the latter is still hot to give a yellow, creamy, homogenous mixture.

After the base is prepared, each of the other ingredients is individually beaten into the base using any suitable mixing device. A simple egg-beater as used in the home is sufficient. Each of the ingredients is added while the mixture is still warm, but there is no need to heat the mixture after the initial heating of the lanolin and petrolatum.

The end product is similar in consistency to a face cream or lotion. Its consistency is more liquid than paste-like, and does not have an oily or greasy feel.

The ingredients listed in the following specific, non-limiting example were added in a like manner to produce a hair pressing cream or composition according to another preferred embodiment of the present invention.

EXAMPLE II

| Ingredient | Amount (fl. oz.) | Parts by Volume |
|---|---|---|
| White Petrolatum | 8 | 32 |
| Anhydrous Lanolin | 8 | 32 |
| Coconut Oil | 1 | 4 |
| Weeping Willow Extract | 1 | 4 |
| Extract of Mustard Greens and Corn | 1 | 4 |
| Glycerine | ¼ | 1 |
| Wheat Germ Oil (Viobin Brand) | 1 | 4 |

The hair pressing cream or composition according to the present invention is used by applying about ½ teaspoon of the cream to the hair and uniformly working it into the hair and scalp. After the composition has been applied to the hair, the hair is dried using a hand blowdryer while continuing to brush the hair. A warm iron is used to seal the composition into the hair fibers. The iron may be a curling iron, a straightening comb or any other suitable styling iron.

A reapplication is desirable approximately every two weeks, but depending on the type and length of hair, climate, etc., the original application may hold the hair for as long as a month or two without requiring a reapplication. After one or two applications of the hair pressing cream of the present invention, it is not necessary to use a hot iron again until several applications later. The hair pressing cream according to the present invention leaves the hair looking and feeling lustrous, shiny and full of body while eliminating the greasy or oily appearance and feel usually associated with the prior art hair pressing creams.

The present invention may be embodied in other specific forms without departing from the spirit or essential attributes thereof and, accordingly, reference should be made to the appended claims, rather than to the foregoing specification, as indicating the scope of the invention.

I claim:

1. In a hair pressing composition having a base comprising a mixture of petrolatum and lanolin, the improvement comprising an effective amount to hold hair in a styled condition and to impart a non-greasy feel and appearance to hair to which said composition is applied of a mixture of weeping willow extract prepared by placing split willow twigs in water, boiling said twigs and said water to form a solution of weeping willow juices in said water, and removing the twigs from said water, said solution being said weeping willow extract, and an extract from mustard greens and corn prepared by mixing together mustard greens with corn kernels, grinding said mustard greens and corn kernels and squeezing the extract from the ground mixture.

2. A hair pressing composition according to claim 1 further comprising minor amounts of glycerine, coconut oil, vinegar and wheat germ oil.

3. A hair pressing cream according to claim 1 comprising a base in an amount of about 56 to 64 parts by volume, said base comprising a mixture of petrolatum and lanolin, and an active constituent comprising from about 4 to 8 parts by volume of said weeping willow extract and about 4 to about 8 parts by volume of said extract from mustard greens and corn.

4. A hair pressing cream according to claim 3, said base further comprising up to about 4 parts by volume of coconut oil, and said active constituent further comprising up to about 1 part by volume each of glycerine and vinegar and from about 1 to about 4 parts by volume wheat germ oil.

5. A hair pressing composition according to claim 1 wherein said weeping willow extract is prepared by placing about 1 part by weight of said twigs in about 20 parts by weight of water, boiling said twigs and said water for a sufficient time to form a solution of weeping willow juices in said water which has the approximate color of tea and removing said twigs from said water, and wherein said extract from mustard greens and corn is prepared by mixing together about 2 parts by weight of said mustard greens with about 1 part by weight of said corn kernels, grinding said mustard greens and said corn kernels and squeezing the extract from the ground mixture.

6. A hair pressing composition comprising about 32 parts by volume of white petrolatum, from about 24 to about 32 parts by volume of anhydrous lanolin, from about 4 to about 8 parts by volume of weeping willow extract prepared by placing split willow twigs in water, boiling said twigs and said water to form a solution of weeping willow juices in said water, and removing the twigs from said water, said solution being said weeping willow extract, and from about 4 to about 8 parts by volume of an extract from mustard greens and corn prepared by mixing together mustard greens with corn kernels, grinding said mustard greens and corn kernels and squeezing the extract from the ground mixture.

7. A hair pressing composition according to claim 6 wherein said lanolin is present in an amount of about 32 parts by volume and said weeping willow extract and said extract from mustard greens and corn are each present in an amount of about 4 parts by volume.

8. A hair pressing composition according to claim 6 wherein said lanolin is present in an amount of about 24 parts by volume, said weeping willow extract and said extract from mustard greens and corn are each present in an amount of about 8 parts by volume.

9. A hair pressing composition according to claim 6 wherein said weeping willow extract is prepared by placing about 1 part by weight of said twigs in about 20 parts by weight of water, boiling said twigs and said water for a sufficient time to form a solution of weeping willow juices in said water which has the approximate color of tea and removing said twigs from said water, and wherein said extract from mustard greens and corn is prepared by mixing together about 2 parts by weight of said mustard greens with about 1 part by weight of said corn kernels, grinding said mustard greens and said corn kernels and squeezing the extract from the ground mixture.

10. A hair pressing composition according to claim 6 further comprising up to about 4 parts by volume of coconut oil, up to about 1 part by volume vinegar, up to about 1 part by volume glycerine and from about 1 to about 4 parts by volume of wheat germ oil.

11. A hair pressing composition according to claim 10 wherein said lanolin is present in an amount of about 32 parts by volume and said weeping willow extract, said extract from mustard greens and corn, said wheat germ oil and said coconut oil are each present in an amount of about 4 parts by volume.

12. A hair pressing composition according to claim 10 wherein said lanolin is present in an amount of about 24 parts by volume, said weeping willow extract and said extract from mustard greens and corn are each present in an amount of about 8 parts by volume, said wheat germ oil and said vinegar are each present in an amount of about 1 part by volume and said coconut oil is present in an amount of about 4 parts by volume.

* * * * *